United States Patent [19]

Takagishi et al.

[11] Patent Number: 4,461,765

[45] Date of Patent: Jul. 24, 1984

[54] SUPPOSITORY CONTAINING SULFAMETHOXAZOLE/TRIMETHOPRIM COMPLEX AND PROCESS FOR PREPARING THE SAME

[75] Inventors: Yasushi Takagishi, Hyogo; Kiichiro Ohsuga, Osaka; Sadao Ohama, Hyogo, all of Japan

[73] Assignee: Shionogi & Co., Ltd., Osaka, Japan

[21] Appl. No.: 288,795

[22] Filed: Jul. 31, 1981

Related U.S. Application Data

[63] Continuation of Ser. No. 112,293, Jan. 15, 1980, abandoned.

[30] Foreign Application Priority Data

Jan. 30, 1979 [JP] Japan ................................. 54-9992

[51] Int. Cl.³ .................. A61K 31/505; A61K 31/625
[52] U.S. Cl. ..................................... 424/229; 424/251; 424/DIG. 15
[58] Field of Search ............... 424/229, 251, DIG. 15

[56] References Cited

U.S. PATENT DOCUMENTS 3,197,369  7/1965  Widmann et al. .......... 424/DIG. 15
3,220,924  11/1965  Tuma ........................... 424/DIG. 15
3,341,541  9/1967  Hoffer ................................. 424/251

FOREIGN PATENT DOCUMENTS 2415660  11/1974  Fed. Rep. of Germany .
805379  12/1975  Japan .

*Primary Examiner*—Allen J. Robinson
*Attorney, Agent, or Firm*—Birch, Stewart, Kolasch & Birch

[57] ABSTRACT

Suppository containing a one-to-one complex of sulfamethoxazole and trimethoprim dispersed in a pharmaceutically acceptable carrier is disclosed. It may contain a supplemental amount of sulfamethoxazole in addition to the sulfamethoxazole component in the complex and is superior to conventional preparations of a simple mixture in its manufacturing process as well as its pharmacokinetical property.

3 Claims, No Drawings

SUPPOSITORY CONTAINING SULFAMETHOXAZOLE/TRIMETHOPRIM COMPLEX AND PROCESS FOR PREPARING THE SAME

This application is a continuation of copending application Ser. No. 112,293, filed on Jan. 15, 1980, now abandoned.

BACKGROUND OF THE INVENTION

1. Field of the Invention

The present invention relates to a suppository, containing as its principal ingredient, a one-to-one complex of sulfamethoxazole and trimethoprim (hereinafter, to be referred to as SMX and TMP, respectively).

A pharmaceutical composition formed by mixing SMX with TMP has been known as an antimicrobial agent which performs an excellent synergetic action (See, for instance, U.S. Pat. No. 3,341,541). It still occupies an important status in the field of treating the particular infectious diseases caused by pathogenic bacteria resistant to other synthetic bactericidal agents and antibiotics. Though an old agent, it still has an irreplaceable importance in the field of chemotherapy.

2. Description of the Prior Art

However, such combination has a large dose as described in the U.S. Pat. No. 3,341,541 (for instance, SMX 800 mg+TMP 160 mg, per day) to make the oral administration difficult as well as to cause some damage to the stomach or duodenum through which this combination agent is absorbed. Therefore, the oral administration thereof is not necessarily easy.

Attempts have hitherto been made to solve the stated problem by administering the mixed preparation through coelomata, for example, the rectum, but a preparation formulated for this purpose by dispersing a simple mixture of SMX and TMP in a carrier has been found unsatisfactory because of its inherent disadvantages which will be stated below.

(1) During the manufacturing process:

In the mixing and kneading operation of the active ingredients with the carrier, the viscosity of the composition will rise abnormally so as to solidify, and this solidifying tendency will make the molding into the required dosage form very difficult.

(2) After preparation:

Uncontrollable variances in physical properties, for example, disintegration, dissolution and melting or softening point are inevitable. These will make the finished dosage form unpreferable from the practical point of view.

In addition to these disadvantages, even with a freshly molded preparation, the blood levels of each of the active ingredients after a predetermined period of administration cannot be attained as expected.

A proposal has been made to overcome these disadvantages in, for instance, German laid-open publication 2,415,660, wherein suppositories comprising two separate layers each containing carrier and one of the active ingredients, SMX or TMP, are disclosed. The separated layers may optionally be isolated further with an insulating layer composed primarily of carrier.

Although the proposed suppository might have overcome at least partly the difficulties ancillary to the manufacturing process, it is obviously inconvenient from the practical point of view because the manufacturing process includes at least two and in some instances three steps to obtain the finished product.

SUMMARY OF THE INVENTION

It is therefore the primary object of the present invention to provide a suppository for chemotherapy containing a one-to-one complex of SMX/TMP, which has overcome the stated disadvantages inherent to the conventional preparations.

Another object of the present invention is to provide a process for preparing the suppositories which may be in the form of a homogeneous mass or rectal capsule composed of a soft capsule filled with a fluid or thixotropic material containing said complex.

Further objects and attendant advantages of the present invention will be made clear to those skilled in the art from the following description of the invention illustrated by way of examples.

According to the present invention, there is provided a suppository comprising as its principal ingredient a one-to-one complex of sulfamethoxazole and trimethoprim dispersed in a pharmaceutically acceptable carrier.

This is based on a discovery of the present inventors that these objects may be accomplished by utilizing said complex, a molecular compound formed by combining SMX with an equimolecular amount of TMP, disclosed in Japanese Pat. No. 805,379 (Publication, No. 20,125/75) which primarily intends to improve the objectionable taste of TMP.

Throughout this specification and claims, the term suppository is used to include a unit dose having a homogeneous solid form at room temperature which melts rapidly in human coelomic ducts, as well as the so-called "rectal capsule" of a unit dose of soft capsule filled with said dispersed substance. The soft capsule is designed to disintegrate in human coelomic ducts to release the ingredient contained therein in a time dependent manner.

The suppository may optionally contain a supplemental amount of sulfamethoxazole in addition to the complex. The amount may range from two to five times as much as that of the sulfamethoxazole component in the complex.

The one-to-one complex is used to mean a molecular compound formed by combining an equimolecular amount of sulfamethoxazole with trimethoprim, as disclosed in the previously described Japanese Patent.

The suppositories are primarily administered through the anus by inserting the same into the sufficient depth of the rectum but may otherwise be administered through any other body coelomic ducts, for example, the vagina as well.

In the other aspect of the present invention, there is provided a process for preparing the stated suppositories characterized in the use of a one-to-one complex of SMX/TMP in lieu of the simple mixture of SMX and TMP.

In the formulating operation, one which is obtained by dissolving an equimolecular mixture of SMX and TMP in a solvent and then removing the solvent by evaporation may likewise be used as the active ingredient in place of the isolated complex of SMX/TMP as is disclosed in the specification of the Japanese Patent.

DESCRIPTION OF THE PREFERRED EMBODIMENTS

The mixing ratio of the established mixture preparation of SMX and TMP, co-trimoxazol (INN) stipulated in Martindale: The Extra Pharmacopeia 27th Ed. pp. 361-2, is fixed to be 5:1 to provide minimum inhibition concentrations of both ingredients of 12 μg/ml and 0.6 μg/ml in the blood level in the case of oral or intravenous administration.

Therefore, a supplemental amount of SMX may optionally be incorporated into the suppository. This is imperative if the blood levels should accurately correspond to the administered amounts with each of the ingredients, and the complex should be equivalent to the simple mixture of SMX and TMP.

It has however been found that the mixing ratio should not necessarily be so rigidly adhered to, because the absorption of the respective ingredients will depend on the species of the agent and the subject to be administered as well as the site of absorption. The absorption of either ingredient through the stomach or intestine may differ from that through the rectum as will be apparent from the later description. No confirmation has hitherto been made on the fixed or parallel relationship among the absorption of SMX through the stomach or intestine, that through the rectum, that of TMP through the stomach or intestine and that through the rectum.

The dose of the suppositories will usually range from 10 to 20 mg/kg of the complex together with a supplemental amount of SMX of about 0–50 mg/kg. The normal period of administration may be from 12 to 18 hours.

The pharmaceutically acceptable carrier may be any carrier or diluent which is conventionally used in preparing suppositories or ointments and having no substantial physiological hazards.

They may be exemplified as, oils of peanuts, palm, olive, soy bean, sesame, cottonseed, castor, linseed, rice bran, rapeseed and corn; fatty oils of cacao butter, tallow and lauric fatty oil; any modified substance of these obtained by hydrogenation, fatty acid moiety substitution or acetylation as well as any esters of saturated fatty acids with polyhydric alcohols.

Water soluble carriers may be exemplified as polyethylene glycol, polypropylene glycol, glycerogelatine, methyl cellulose and carboxymethyl cellulose.

Any surfactant having only a mild action to biomembranes may equally be incorporated into the preparation of the present invention in order to improve or promote the absorption of the active ingredients through the membrane. Of these surfactants, polyoxyethylenesorbitan fatty acid esters, polyoxyethylenesorbitol fatty acid esters, polyoxyethylene fatty acid esters, glycerine fatty acid esters as well as polyoxyethylene higher alcohol esters are exemplified as non-ionic surfactants.

Esters of alkylsulfonic acid and esters of polyoxyethylene alkyl sulfonate may be incorporated as anionic surfactants. Polyoxyethylene alkylamine or its amides are suitable cationic surfactants.

In addition to these, a suitable emulsifier, dispersing agent, viscosity adjusting agent, stabilizer, and coloring agent may optionally be incorporated into the suppositories in accordance with the requirements.

In the following paragraphs, the present invention will be illustrated in further detail by referring to the preferred embodiments.

Example 1. (Suppository)

1. Manufacturing process:

The carrier, Witepsol (Registered Trademark of Dynamit Nobel A.G., West Germany: a mixture of mono-, di- and tri-glycerides of $C_{12}$–$C_{18}$ saturated fatty acid) was melted at 50° C. and the active ingredients were added thereto in accordance with the mixing ratios in Table I below, respectively while being stirred to be uniformly and evenly dispersed in the carrier. The dispersion was subdivided and cooled for molding into homogeneous solid masses, each having 1 g weight to obtain the intended dosage forms.

TABLE I

| (Active ingredients) | (Carrier) | A (Invention) | B (Invention) | C (Control) | D (Control) |
|---|---|---|---|---|---|
| SMX/TMP complex | | 15 | 15 | | |
| SMX | | | | 33 | 7 | 40 |
| TMP | | | | | 8 | 8 |
| | Witepsol | 85 | 52 | 85 | 52 |
| (Total) | | 100 | 100 | 100 | 100 |

(In each of the formulae, the molar ratio of TMP is kept constant while those of others are varied)

2. Measurements of melting points:

The results of the measurement conducted in compliance with the second method stipulated in Japan Pharmacopeia 9th Ed., with the freshly molded dosage forms and the ones aged at 30° C. for one month are summarized in Table II.

TABLE II

| (°C., average of 6 pieces) | | | | |
|---|---|---|---|---|
| | Formula | | | |
| | A | B | C | D |
| (Freshly molded) | 36.0 | 36.3 | 36.8 | 37.5 |
| (Aged at 30° C. for 1 month) | 36.5 | 36.8 | 37.5 | 38.8 |

3. Dissolution:

The measurements of the dissolution rate were performed in compliance with the paddle method stipulated in U.S. Pharmacopeia 4th Ed., Supplements, with the fresh and aged ones. Ingredients dissolved in distilled water (900 ml), 60 minutes after the immersion at 37° C. and 100 r.p.m. were determined to be summarized in the following Table III.

TABLE III

| (%, average of 6 pieces) | Ingredient determined. | Formula | | | |
|---|---|---|---|---|---|
| | | A | B | C | D |
| (Freshly molded) | SMX | 72.1 | 65.0 | 55.9 | 40.5 |
| | TMP | 72.5 | 60.0 | 51.2 | 25.9 |
| (Aged at 30° C. for 1 month) | SMX | 65.3 | 58.3 | 30.7 | 20.3 |
| | TMP | 67.2 | 55.5 | 32.3 | 18.8 |

(Quantitative determinations of SMX were performed by High Performance Liquid Chromatography, while those of TMP were performed by Gas Chromatography).

4. Plasma levels after rectal administration in dogs:

The freshly molded suppositories (each 1 g) of Formula A, B, C and D were used in this study for evaluating the rectal absorption of the active ingredients.

Each of five male beagles (average weight, 10 kg) had been fasted for 17 hours and evacuated before being inserted with the suppositories into their recta at 4 cm depth from the anus.

Blood samples were taken from paw vasculars at each sampling time and centrifuged to obtain the plasma for the evaluation. The quantitative determinations of the active ingredients were made in accordance with the method as previously described to obtain the result summarized in Table IV.

TABLE IV

| Formula | Ingredient | Plasma levels (μg/ml) after administration | | | | | | | | |
|---|---|---|---|---|---|---|---|---|---|---|
| | | 0.5 | 1 | 2 | 3 | 5 | 7 | 9 | 12 | 24 (hr) |
| A | SMX | 4.0 | 6.8 | 31.4 | 43.9 | 40.9 | 41.2 | 33.8 | 18.4 | 5.9 |
| | TMP | 0.50 | 1.10 | 1.20 | 0.98 | 1.00 | 1.05 | 0.90 | 0.60 | 0.25 |
| B | SMX | 18.1 | 15.1 | 67.4 | 73.6 | 75.0 | 77.9 | 70.1 | 58.2 | 20.1 |
| | TMP | 0.33 | 0.75 | 0.84 | 0.91 | 1.15 | 1.20 | 1.05 | 0.82 | 0.35 |
| C | SMX | 1.2 | 3.9 | 11.9 | 24.9 | 30.2 | 28.7 | 25.5 | 15.7 | 1.3 |
| | TMP | 0.33 | 0.78 | 0.75 | 0.81 | 0.75 | 0.69 | 0.55 | 0.46 | 0.16 |
| D | SMX | 3.0 | 14.3 | 35.0 | 48.1 | 45.2 | 44.9 | 44.8 | 39.3 | 7.1 |
| | TMP | 0.18 | 0.33 | 0.39 | 0.42 | 0.48 | 0.54 | 0.48 | 0.48 | 0.12 |

In performing the experiments whose results are briefly presented, the following facts are confirmed to support the unpredictable advantages of the present invention over the prior art, together with the results themselves.

(1) Moldability:

In the manufacturing process of the products in accordance with the formulae A and B, a conventional manner customary for the preparation of suppositories was able to be applied without any difficulty and without requiring any substantial modification, by virtue of the suitable fluidity maintained throughout the kneading operation.

With the products of the formulae C and D, however, the viscosities of the mixture had risen abnormally during the dispersing and kneading operations to result in a premature solidification. This abnormal tendency in the rising viscosity and solidification made the casting of the dispersion into molds very difficult and in some instances almost impossible.

(2) Melting Point:

With the freshly molded products, both sets of suppositories melted around body temperature. With the aged products, however, the suppositories of the formulae C and D, showed remarkable rises in melting point as compared with those of the formulae A and B. Rise in melting point means the corresponding prolongation in melting time in coelome to make the product unacceptable. In general, a rise in melting point of a suppository by one degree centigrade around the body temperature may well be taken as a serious fatal disadvantage which would make the practical application of the product impossible.

(3) Dissolution:

All of the products of the formulae C and D were found to be inferior to those of A and B in their dissolution properties, even in the freshly molded ones not to mention the aged ones.

It was found that the aged products of the formulae C and D were so seriously deteriorated that they were unable to be put into practical use.

(4) Absorption through rectum:

The products of formula A brought about concentrations in blood levels of the respective ingredients about 1.5-2 times as high as that brought about by that of the formula C in the same effective dose. Similar results were observed in a comparison of the product of the formula B with that of D.

Obviously, this property is closely associated with the melting point and dissolution. It is recognized that there is no need to further confirm the difference between the aged products of the formulae C and D and those of A and B.

From the stated facts and analysis, it is safely concluded that a satisfactory bactericidal action can be expected by administering the preparation of the complex in a dose of about 15 mg/kg, in an administration period of from 12 to 18 hours.

Example 2. (Rectal Capsule)

(1) Manufacturing process:

In accordance with the compounding ratios in Table V below, polyoxyethylene oleyl ether is dispersed into sesame oil at 40° C. To this dispersion the active ingredients were added under stirring to obtain a uniform suspension. This was subdivided into portions each containing one gram for encapsulation in a soft gelatine capsule.

TABLE V

| | | Formula (g) | |
|---|---|---|---|
| (Active ingredients) | (Carrier) | E (Invention) | F (Control) |
| SMX/TMP complex | | 30 | |
| SMX | | | 80 |
| TMP | | | 16 |
| | Sesame oil | 94 | 94 |
| | Polyoxyethylene oleyl ether | 10 | 10 |
| Total | | 200 | 200 |

In the dispersing and kneading operation, the fluidity of the suspension in sesame oil in the formula F was lost to show a solidifying tendency to make the filling operation difficult. In that of the formula E, the fluidity was maintained satisfactorily throughout the operation to ensure an easy encapsulation.

(2) Disintegration:

Experiments were performed on the soft capsules obtained above, in accordance with the test method for capsule disintegration stipulated in Japan Pharmacopeia 9th Ed, wherein distilled water was employed as the test liquid in place of the artificial gastric juice, to obtain the disintegrations (expressed in terms of time required for the disintegration in minutes) described in Table VI.

TABLE VI

| Formula | Freshly molded | Aged at 30° C. for one month |
|---|---|---|
| E | 10-15 | 15-20 |
| F | 60-70 | over 120 |

The product of the formula E suffered no substantial aging effect and showed a satisfactory disintegration. That of the formula F was subjected to considerable deterioration in the manufacturing process to show an abnormally prolonged disintegration time even after being freshly molded, and it was found that the practical service of this product is substantially impossible because it did not disintegrate for as long as 120 minutes.

What is claimed is:

1. A method for treating infectious diseases caused by pathogenic bacteria comprising the step of:

inserting into the rectum of a subject suffering from an infectious disease a suppository comprising an effective antibacterial amount of a one-to-one complex of sulfamethoxazole and trimethoprim and an effective antibacterial supplemental amount of sulfamethoxazole in addition to the complex in a pharmaceutically acceptable carrier which is in solid form at room temperature but which melts rapidly in human coleomic ducts in a unit dosage form suitable for rectal administration to thereby achieve increased absorption of the active ingredients.

2. A method according to claim 1, wherein said supplemental amount is two to five times as much as that of the sulfamethoxazole component in the complex.

3. A method according to claim 1, wherein said complex is administered in a dose range of from 10 to 20 mg/kg of the complex.

* * * * *